(12) United States Patent
Compadre et al.

(10) Patent No.: US 7,541,045 B2
(45) Date of Patent: *Jun. 2, 2009

(54) CONCENTRATED, NON-FOAMING SOLUTION OF QUATERNARY AMMONIUM COMPOUNDS AND METHODS OF USE

(75) Inventors: Cesar Compadre, Little Rock, AR (US); Philip Breen, Little Rock, AR (US); Hamid Salari, Wayne, NJ (US); E. Kim Fifer, North Little Rock, AR (US); Danny L. Lattin, Brookings, SD (US); Michael Slavik, Springdale, AR (US); Yanbin Li, Fayetteville, AR (US); Timothy O'Brien, Little Rock, AR (US); Amy L. Waldroup, Springdale, AZ (US); Thomas F. Berg, Sheboygan, WI (US)

(73) Assignee: University of Arkansas, Little Rock, AR (US)

(*) Notice: Subject to any disclaimer, the term of this patent is extended or adjusted under 35 U.S.C. 154(b) by 0 days.

This patent is subject to a terminal disclaimer.

(21) Appl. No.: 10/943,217

(22) Filed: Sep. 17, 2004

(65) Prior Publication Data

US 2005/0113012 A1    May 26, 2005

Related U.S. Application Data

(60) Division of application No. 09/494,374, filed on Jan. 31, 2000, now Pat. No. 6,864,269, which is a continuation-in-part of application No. 08/840,288, filed on Apr. 14, 1997, now Pat. No. 6,039,992, which is a continuation-in-part of application No. 08/631,578, filed on Apr. 12, 1996, now Pat. No. 5,855,940.

(51) Int. Cl.
*A01N 25/02* (2006.01)

(52) U.S. Cl. ............... 424/405; 424/78.07; 424/406; 514/315; 514/358; 514/408; 426/326; 426/332; 426/335; 426/532

(58) Field of Classification Search ............... 514/315, 514/358, 408
See application file for complete search history.

(56) References Cited

U.S. PATENT DOCUMENTS 2,756,647 A    7/1956   Thompson (Continued)

FOREIGN PATENT DOCUMENTS

AU           735308          10/2000

(Continued)

OTHER PUBLICATIONS

Breen, et al. *J. Food Sciences*, 60:1191-1196 (1995).

(Continued)

*Primary Examiner*—Neil Levy
(74) *Attorney, Agent, or Firm*—Foley & Lardner LLP

(57) ABSTRACT

A concentrated quaternary ammonium compound (QAC) solution comprising a QAC with a concentration from greater than about 10% by weight and at least one solubility enhancing agent, such as an alcohol, is disclosed. A diluted QAC solution is used to contact food products to prevent microbial growth on the food products from a broad spectrum of foodborne microbial contamination. A method of contacting the food products with the dilute QAC for an application time of at least 0.1 second is disclosed. The foods that can be treated by this method are meat and meat products, seafood, vegetables, fruit, dairy products, pet foods and snacks, and any other food that can be treated and still retain its appearance and texture. One of the treatment methods is spraying and misting the QAC solutions on the food products for an application time of at least 0.1 second to prevent broad spectrum foodborne microbial contamination.

21 Claims, 5 Drawing Sheets

U.S. PATENT DOCUMENTS

| | | | |
|---|---|---|---|
| 3,036,084 | A | 5/1962 | Duennenberger et al. |
| 3,787,566 | A | 1/1974 | Gauvreau et al. |
| 4,165,375 | A | 8/1979 | Berger et al. |
| 4,205,061 | A | 5/1980 | Vidra |
| 4,472,373 | A | 9/1984 | Ryan |
| 5,030,659 | A | 7/1991 | Bansemir et al. |
| 5,084,096 | A | 1/1992 | Stovicek |
| 5,366,983 | A | 11/1994 | Lattin et al. |
| 5,405,604 | A | 4/1995 | Hall |
| 5,414,124 | A | 5/1995 | Smith et al. |
| 5,454,984 | A | 10/1995 | Graubart et al. |
| 5,518,636 | A | 5/1996 | Petrille, III et al. |
| 5,520,575 | A | 5/1996 | Dickson |
| 5,693,315 | A | 12/1997 | Bevilacqua |
| 5,712,290 | A * | 1/1998 | Schmidt et al. ............ 514/311 |
| 6,001,864 | A * | 12/1999 | Akashi et al. ............... 514/399 |
| 6,136,776 | A | 10/2000 | Dickler et al. |
| 6,248,343 | B1 * | 6/2001 | Jampani et al. ............. 424/405 |

FOREIGN PATENT DOCUMENTS

| | | |
|---|---|---|
| CA | 1 154 555 | 10/1983 |
| DE | 24 50 666 A1 | 4/1976 |
| DE | 32 33 607 A1 | 3/1984 |
| DE | 43 21 566 A1 | 1/1995 |
| DE | 198 29 743 A1 | 1/2000 |
| EG | 22162 | 9/2002 |
| EP | 0 119 226 B1 | 9/1984 |
| EP | 0 534 887 B1 | 3/1993 |
| EP | 0 912 101 | 5/1999 |
| GB | 479925 | 5/1936 |
| JP | 91-321575 | 10/1991 |
| JP | 2000-508541 | 7/2000 |
| WO | WO 91/04668 A1 | 4/1991 |
| WO | WO 95/17159 A1 | 6/1995 |
| WO | WO 97/27880 A1 | 8/1997 |
| WO | WO 97/38586 A1 | 10/1997 |
| WO | WO 98/03066 A1 | 1/1998 |
| WO | WO 01/54502 A2 | 8/2001 |

OTHER PUBLICATIONS

Breen, et al. Presented at "New Technology to Improve Food Safety" Conference (Apr. 13, 1995).

Dorsa, et al. "Effects of Acetic Acid, Lactic Acid and Trisodium Phosphate on the Microflora of Refrigerated Beef Carcass Surface Tissue Inoculated with *Escherichia coli* 0157:H7, Listeria innocua, and Clostidium sporogenes"; Journal of Food Protection, vol. 60, No. 6, 1997, pp. 619-624.

Somers, et al. *Int. J. Food Microbiol*, 22:269-276 (1994).

Thomas, et al. "Factors which affect retention of Salmonella by chicken muscle fascia", *Biofouling*, 5:75-87 (1991).

Wang, et al. "Bacterial Penetration into Eggs Washed with Various Chemicals and Stored at Differenct Temperatures and Times"; Journal of Food Protection, vol. 61, No. 3, 1998, pp. 276-279.

Chemical Abstract XP-002170743 (Yang, et al. "Use of Antimicrobial Spray Applied with an Inside-outside Bird-washer to Reduce Bacterial Contamination on Precilled Chicen Carcasses", *J. Food Prot*. vol. 61, No. 7, 1998, pp. 829-832).

Dorsa, W.. "New and Established Carcass Decontamination Procedures Commonly Used in the Beef-Processing Industry"; Journal of Food Protection, vol. 60, No. 9, 1997, pp. 1146-1151.

Siragusa, G. "The Effectiveness of Carcass Decontamination Systems for Controlling the Presence of Pathogens on the Surfaces of Meat Animal Carcasses"; HACCP: An Integrated Approach to Assuring the Microbiological Safety of Meat on Poultry, Sheridan, Buchanan, and Montville, 1996, pp. 89-98.

Wang, et al. "Trisodium Phosphate and Cetylpyridinum Chloride Spraying on Chichen Skin to Reduce Attached *Salmonella typhimurium*"; Journal of Food Protection, vol. 60, No. 8, 1997, pp. 992-994.

AN 1968:43156 Caplus Abstracts.

AN 1971:86344 Caplus Abstracts.

AN 1973:417711 Caplus Abstracts.

AN 1990:426739 Caplus Abstracts.

AN 69(05):C0205 Food Science and Technology Abstracts.

AN 89(11):C0023 Food Science and Technology Abstracts.

Ayers, et al. *Microbiology of Foods*, W.H. Freeman and Company, Chapter 6, pp. 123-135(1980).

Ciosek, et al. *Med. Weter.*, 40:335, 338 (1984); Chem. Abst. 101:187892m.

Dalgaard, et al. "Specific Inhibition of Photobacterium phosphoreum Extends the Shelf Lift of Modified-Atmosphere-Packed Cod Fillets"; Journal of Food Protection, vol. 61, No. 9, 1998, pp. 1191-1194.

Delazari, et al. "Decontaminating Beef for *Escherichia coli* 0157:H7"; Journal of Food Protection, vol. 61, No. 5, 1998, pp. 547-550.

Dorsa, et al. "Long-Term Effect of Alkaline, Organic Acid, or Hot Water Washes on the Microbial Profile of Refrigerated Beef Contaminated with Bacterial Pathogens after Washing"; Journal of Food Protection, vol. 61, No. 3, 1998, pp. 300-306.

Fisher, et al. "Fate of *Escherichia coli* 0157:H7 in Ground Apples Used in Cider Production"; Journal of Food Protection, vol. 61, No. 10, 1998, pp. 1372-1374.

Harvey, S.C. "Antimicrobial Drugs" in Remington's *Pharmaceutical Sciences*, 18th Ed., Mack Publishing Co., pp. 1163-1164 (1990).

Kim, et al. *J. Infect. Dis.*, 170:1606-1609 (1994).

Kotula, et al. "Reduction of Aqueous Cholorine by Organic Material"; Journal of Food Protection, vol. 60, No. 3, 1997, pp. 276-282.

Lattin, et al. In 1993-1994 Food Safety Research Progress Report, pp. 66-70.

Lonza Bardac—2050 Product Sheet (2000).

Mustapha, et al. "Destruction of Listeria monocytogenes by Sodium Hypochlorite and Quaternary Ammonium Sanitizers"; Journal of Food Protection, vol. 52, No. 5, May 1989, pp. 306-311.

Merck Index (The), 1983, pp. 1130-1131.

Ray, B. "Table of Contents", Fundamental Food Microbiology, 1996.

Salton, et al. "Structure" in *Medcial Microbiology*, 3rd Ed., Churchill Livingston, pp. 37-54 (1991).

Slavik, et al. In 1993-94 Food Safety Progress Report, pp. 8-12.

\* cited by examiner

US 7,541,045 B2

CONCENTRATED, NON-FOAMING SOLUTION OF QUATERNARY AMMONIUM COMPOUNDS AND METHODS OF USE

This application is a divisional of U.S. Ser. No. 09/494,374, filed Jan. 31, 2000, now U.S. Pat. No. 6,864,269 which is a continuation-in-part of U.S. Ser. No. 08/840,288 filed on Apr. 14, 1997, now U.S. Pat. No. 6,039,992, which is a continuation-in-part of U.S. Ser. No. 08/631,578 filed on Apr. 12, 1996, now U.S. Pat. No. 5,855,940, all of which are herein incorporated by reference in their entirety.

BACKGROUND OF THE INVENTION

1. Field of Invention

The present invention relates to a solution comprising a concentrated amount of an antimicrobial quaternary ammonium compound (QAC). The QAC concentrate of the present invention utilizes GRAS (generally recognized as safe) components to form a true solution, not an emulsion, of the QAC. This QAC concentrate solution is prepared in combination with at least one solubility enhancing agent and is useful in preparing solutions for dilution to a final concentration that are useful in industrial food processing or in the home in food preparation and on surfaces associated with food processing.

The present invention relates generally to a solution comprising a concentrated amount of an antimicrobial QAC and at least one solubility enhancing agent that is suitable for use in methods of preventing the growth of a broad range of microorganisms on and in food products, as well as on surfaces that come in contact with food products in the home or in an industrial environment. More specifically, the present invention relates to a solution comprising a concentrated amount of an antimicrobial QAC and at least one solubility enhancing agent that is suitable for use in a method for preventing the growth of a broad spectrum of microorganisms on and in food products; by contacting such food products, as meat products, for example, poultry, beef, pork, lamb, venison, and other edible meat products; seafood, for example, fish and shellfish; fruit, vegetables, dairy products, pet foods or snacks, such as those prepared from animal meat, skin and parts, that may include pig's ears, rawhide and jerky; and any other food products that can be treated utilizing the aqueous treatment methods of the present invention without detrimentally affecting the appearance, texture, and quality of the food. More specifically, the present invention relates to a solution comprising a concentrated amount of an antimicrobial QAC that is suitable for use in a method to inhibit the attachment of, to remove, and/or to prevent the growth of microorganisms on food products. Particularly, the use of the solution comprising a concentrated amount of an antimicrobial QAC relates to the effect of QACs on microorganisms that can cause foodborne contamination. More particularly, these microorganisms include microorganisms from the genus *Staphylococcus, Streptococcus, Campylobacter, Arcobacter, Listeria, Aeromonas, Bacillus, Salmonella*, non-toxin-producing *Escherichia*, pathogenic toxin-producing *Escherichia*, such as O157:H7. More particularly, the present invention relates to an improved treatment method of applying diluted QACs on food products, by any means, but preferably includes spraying or misting diluted QACs on the food products to prevent broad spectrum microbial growth on these products, where the application time of the QAC can be as short as at least one tenth of a second. This short application time of the dilute QAC is particularly useful in a commercial or industrial setting.

2. Description of the Prior Art

Prevention of foodborne illnesses by microbial contamination is of major concern to the food processing industry, regulatory agencies, and consumers. A recent report from the Food Safety & Inspection Service (FSIS) of the United States Department of Agriculture (Federal Register, Feb. 3, 1995) estimates that over 2 million cases of foodborne illnesses are produced annually by microbial contamination in the United States, with an associated cost of over $1 billion. Foodborne microbial contamination occurs both prior to entry into the processing facility, and by cross-contamination in the processing environment. The FSIS has instituted new Hazard Analysis and Critical Control Point (HACCP) requirements to reduce the occurrence and number of foodborne pathogens. These regulations must be met by food processors. Although the means of achieving this microbial reduction is left to the discretion of the processor, FSIS expects that antimicrobial treatments will be an important component of HACCP plans. The treatment methods of the present invention, which employ aqueous formulations prepared from solutions of concentrated QACs, are useful in meeting the HACCP requirements.

In their efforts to provide a product completely free of microbial contamination, poultry and meat processors have encountered major difficulties in removing microorganisms that adhere or attach vigorously to poultry and meat tissues intended as food products. If contaminating microorganisms do not attach to the surface of the food, they can be easily rinsed off. However, the microorganisms that become strongly attached cannot be removed by rinsing and are quite resistant to removal by chemical or physical means.

Several chemical and physical methods have been proposed to reduce microorganisms in meat products, such as the use of chlorine or chlorine dioxide, ozone, hydrogen peroxide, lactic acid, sodium carbonate, trisodium phosphate, and electrical stimulation. Generally, these methods have shown limited effectiveness in reducing microbial contamination and may affect the physical appearance of the meat products.

*Salmonella typhimurium* contamination has been of special concern to the poultry processing industry because the organism is often present on live birds. Poultry processors have had great difficulty in removing microorganisms, such as *S. typhimurium*, that attach or adhere to poultry tissues. A variety of chemical and physical approaches have been suggested for use during poultry processing to eliminate *S. typhimurium* contamination of carcasses and minimize cross-contamination among carcasses. Trisodium phosphate (TSP) has been utilized in poultry processing for suppressing *S. typhimurium*; however, studies report conflicting results on the efficacy of TSP against *Salmonella*. As a result of its water solubility, TSP can be washed off of the poultry and thus, cannot inhibit attachment of microorganisms.

U.S. Pat. No. 5,366,983, incorporated herein by reference, discloses a method for removing or preventing *Salmonella* contamination of meat products by treatment with an effective amount of an aqueous solution of a QAC. Specifically, quaternary ammonium cationic surfactants, such as alkylpyridinium, particularly cetylpyridinium chloride (CPC) and cetylpyridinium bromide (CPB) were effective in removing *S. typhimurium* from poultry. This patent, however, does not disclose that QACs have a broader antimicrobial spectrum against any other genuses of food contaminating microorganisms than *Salmonella*. Further, it does not suggest that this treatment method would be effective on food products other than meat. Additionally, it does not suggest that very short QAC application times can be utilized and still provide effective antimicrobial treatment. Nor does it suggest solutions of concentrated QACs, as disclosed in the present invention, that are particularly useful in preparing dilute QAC solutions.

Food substances differ chemically and physically by virtue of their protein content, porosity, lipophilicity, surface pH, water permeability, surface area, and surface net electrical charge. Porosity of food could be important in the sequestration of bacteria whereas a tough, impermeable integument on a food substance could reduce bacterial contamination of the food. All of these chemical and physical differences among food products make it difficult to predict whether one antimicrobial agent's success on meat products would suggest success on other food products, such as fruit, vegetables, seafood, dairy products, and pet foods or snacks.

For example, the QAC, CPC, is known to bind to proteins; however, if the antimicrobial efficacy of CPC on food products was due in large part to the protein binding, then the present method for treating non-proteinaceous fruits and vegetables would not have been expected to be successful.

Increasingly, foodborne illnesses caused by other pathogenic and spoilage bacteria than *Salmonella* have become a problem for food processors. A list of these bacteria with the products, in which they have been identified, is presented in Table 1:

TABLE 1

INCIDENCE OF PATHOGENIC AND SPOILAGE BACTERIA

| Microorganism | Poultry | Beef | Pork | Pathogen | Spoilage |
|---|---|---|---|---|---|
| Aeromonas hydrophila | X | X | X | | X |
| Arcobacter butzleri | | X | X | X | |
| Bacillus cereus | X | X | X | X | |
| Campylobacter jejuni | X | X | X | X | |
| Escherichia coli O157:H7 | X | X | X | X | |
| Listeria monocytogenes | X | X | X | X | |
| Salmonella typhimurium | X | X | X | X | |
| Staphylococcus aureus | X | X | X | X | |

Among these contaminating microorganisms listed in the table, *Escherichia coli* O157:H7 is of special concern because of its virulence, severity of the illness produced, and associated mortality. *E. coli* O157:H7 produces strong "shiga-like" toxins that lead to blood clotting abnormalities, kidney failure (hemolytic uremic syndrome), and death. Even if recovery from the acute illness is complete, 15-30% of infected people with hemolytic uremic syndrome will have evidence of chronic kidney disease. The risks associated with contamination with *E. coli* O157:H7 are compounded by its reported resistance to antibiotics. In 1993, between 8,000-16,000 cases of foodborne illnesses were produced by *E. coli* O157:H7 with an estimated cost of between 0.2 and 0.5 billion dollars.

Another virulent food contaminant, *Listeria monocytogenes* has been found in meat, vegetables, and various milk products; and may cause sepsis, meningitis, and disseminated abscesses. *L. monocytogenes* is a cold tolerant microorganism capable of growing under refrigeration. In 1993, about 1,700 cases of foodborne illness were produced by *L. monocytogenes* with an estimated cost of between 0.1 and 0.2 billion dollars.

Another microorganism of concern in the food industry is *Aeromonas hydrophila* which causes spoilage in the food and meat processing industry and reduces the shelf life of these products.

Presently, there are no known microbiocidal compounds which are effective at preventing and removing contamination in a broad range of food products against a broad spectrum of gram positive, gram negative, aerobic, facultative anaerobic, and microaerophilic microorganisms. The present inventors have determined that QACs are effective against a broad spectrum of different microorganisms which produce foodborne illnesses when they become attached to a broad range of food products. This sensitivity of a broad spectrum of pathogenic microorganisms could not have been predicted.

Sensitivity of a microorganism to a particular antimicrobial agent is not predictive of the sensitivity of other microorganisms to the same agent. It is believed that antiseptics or germicides have a continuous spectrum of activity but the relative susceptibilities of different microorganisms must be considered. For example, the germicide, hexachlorophene is primarily effective against Gram positive microorganisms, and cationic antiseptics are not effective against sporulating organisms. Some Gram negative microorganisms, such as *Pseudomonas cepacia*, have been known to grow in solutions of the drug, benzalkonium chloride. Other bacteria have been known to be capable of growing in 70% ethanol (Harvey, S. C., *Antimicrobial Drugs* in Remington's *Pharmaceutical Sciences*, 18th Ed., Mack Publishing Co., pp. 1163-1241 1990).

In regard to the treatment of food products, it has been reported that *Listeria* is more resistant to the action of TSP than *Salmonella* or *E. coli* (Somers, E. B. et al., *Int. J. Food Microbiol.*, 22:269-276, 1994). Further, (Breen et al., *J. Food Sciences*, 60:1991-1996, 1995) demonstrated that TSP is much less effective in inhibiting *Salmonella* growth than it is in detaching this organism. Similarly, TSP has reduced the numbers of *E. coli* O157:H7 on chicken carcasses but is ineffective in inhibiting the cross-contamination of this microorganism to other chickens.

The present invention shows that QACs are effective against *E. coli* O157:H7 in suspension in liquids, in reducing the numbers of this bacteria when it is attached to food products, as well as in inhibiting the attachment of this bacteria to food products. It has been reported that *E. coli* O157:H7 shows resistance towards broad spectrum antimicrobial agents, such as tetracycline, streptomycin, sulfisoxazole (Kim et al., *J. Infect. Dis.*, 170:1606-1609, 1994) and oxytetracycline (Ciosek et al., *Med. Weter.* 40:335,338:1984), whereas these same agents are very active against regular non-toxin-producing strains of *E. coli*.

Clearly the effectiveness of an antimicrobial agent or biocide against a particular microorganism cannot be predicted based upon its effectiveness against a different microorganism. There are many factors to consider, such as microbial characteristics, which may play a role in the effectiveness of an antimicrobial agent against a particular microorganism. These characteristics may include but are not limited to: (1) the degree of glycocalyx formation by a given species of attached microorganism, (2) the presence of a lipopolysaccharide- and phospholipid-containing cell envelope in gram negative bacteria, (3) the presence of lipoprotein as in most enteric bacteria and *Pseudomonas*, and (4) the presence of porin protein channels, for example in *E. coli* and *Salmonella* (Fulton et al., *Structure* in *Medical Microbiology*, 3rd Ed., pp. 37-54, 1991).

The food processing industry, as well as home, restaurant or institutional food preparation, is in need of more effective products and processes for the prevention of growth of a broad range of contaminating microorganisms on many different food products and/or surfaces that the food products and juices or liquids from the food come in contact. This is especially true for microorganisms which are attached to the surfaces of food. As a result of increasing numbers of illnesses caused by foodborne pathogenic microorganisms, the food processing industry now requires more effective processes for the removal and prevention of a broader spectrum of microorganisms, and particularly for pathogenic microorganisms, such as, toxin-producing *Escherichia*, i.e., *E. coli* O157:H7, which are known to cause serious human diseases as a result of food contamination. The present invention provides a composition comprising a solution of concentrated QAC and at least one solubility enhancing agent and methods of preventing the growth of microorganisms on and in the food, as well as, in liquids and on surfaces associated with food products and their preparation. This method of prevention is an important goal in preventing cross-contamination from infected food products; in removing attached microorganisms from food products, in inhibiting the attachment of microorganisms to the food products; and in preventing the growth of microorganisms that remain attached to the food products. Further, the method of the present invention can easily be adapted for use in a food processing plant.

Additionally, the present invention provides compositions comprising a solution comprising a concentrated amount of QAC in combination with at least one solubility enhancing agent or solvent. This concentrated QAC solution of the present invention provides a stock solution from which dilute compositions of QACs can be prepared for treatment of food products and surfaces associated with food product processing and preparation, including the bodies of animals from which the food product is prepared. For example, the teats of dairy cows can be treated with a dilute solution of the concentrated QAC solution prior to milking, to enhance the safe processing of the milk and milk products. Additionally, a dilute solution of QAC may be useful for washing hands and bodies of humans and pets, with the components described herein or in combination with other components known to be useful hand and body washes. The concentrated QAC solutions are useful in preparing dilute working solution for use in the present method. The formulations of the present invention contain solubility enhancing components which allow more concentrated compositions of QACs to be prepared.

U.S. Pat. No. 5,405,604 discloses a concentrated mouth rinse, methods of use and methods of manufacturing the mouth rinse. The mouth rinse is composed of a concentrated composition in the form of an oil-in-water emulsions that consists essentially of from about 0.05% to about 10.0% of a QAC; from about 30% to about 85% of a solvent that acts as a carrier for flavoring oil, where the solvent is propylene glycol, polyethylene glycol and mixtures thereof; from about 0.2% to about 9.0% of a flavoring oil and water. The composition of the present invention differs from the mouth rinse composition by containing greater than 10% QAC, by being a true homogenous solution rather than an emulsion and by not containing flavoring oils.

WO 98/03066 discloses an antimicrobial composition, methods of preparation and methods of use. The composition is composed of subcomponent a) a substituted or unsubstituted $C_1$-$C_4$ monocarboxylic acid approximately 50-99.9% by weight and subcomponent b) a microbiocidal or microbiostatic cationic organic nitrogen compound approximately 0.1-50% by weight. The composition of the present invention differs from this composition of WO 98/03066, in that it does contain a solubility enhancing agent and WO 98/03066 does not. The present invention differs from WO 98/03066, in that it does not contain an organic acid, such as a monocarboxylic acid, and specifically does not contain a substituted or unsubstituted $C_1$-$C_4$ monocarboxylic acid which is the primary component of the composition of WO 98/03066. The disclosure of WO 98/03066 recites that the efficacy of antimicrobial unsubstituted $C_1$-$C_4$ monocarboxylic acid containing compositions against *Salmonella* can be enhanced by adding a cationic organic nitrogen compound. It is a theory of this invention that a cationic microbiocidal nitrogen compound is better able to exert its effect in microbes damaged by $C_1$-$C_4$ carboxylic acids. The compositions of this invention can additionally contain an additional organic acid that mixes with the cationic organic nitrogen compound to form an "ancat" or "catan" compound, which is not present in the composition of the present invention.

SUMMARY OF THE INVENTION

The concentrated QAC solution of the present invention provides a concentrated antimicrobial solution that is easily diluted to a solution, that is contacted with food products, and surfaces associated with food products, including portions of live or dead animals, in the case of food products obtained from animals. The concentrated QAC solution of the present invention comprises a QAC and at least one solubility enhancing agent. Preferably the QAC is in a concentration of greater than about 10% by weight. The concentrated solution is diluted to provide a dilute growth inhibiting effective amount of QAC in an aqueous solution with the diluted solubility enhancing agent. QACs of the present invention are effective in preventing the growth of a broad spectrum of pathogenic and spoilage microorganisms. QACs, particularly cetylpyridinium chloride (CPC), are especially effective in preventing the growth of a broad spectrum of microorganisms on a broad range of food products.

The present invention provides a method for preventing growth of microorganisms on food products comprising contacting a food product with a microbial growth inhibiting effective amount of QAC for the prevention of growth of a broad spectrum of microorganisms on food products, where the application time of the compound on the food product is for at least a fraction of a second. The prevention of growth of microorganisms on food products is intended to provide a food product that is devoid of or contains minimal numbers of viable microorganisms that could cause illness in humans or animals or spoilage of the food product prior to ingestion. The prevention of growth of microorganisms on food products is intended to include but is not limited to the following mechanisms: (1) removal of attached microorganisms from the food products; (2) inhibition of attachment of microorganisms to the food products; (3) killing or inactivation of attached microorganisms on the food products; and (4) killing or inactivation of microorganisms which are not attached to the food product but which are present in liquids associated with the food products during processing; such as in chill tanks, or which are present on surfaces associated with food preparation, liquids remaining on such surfaces, such as countertops, cutting boards and sinks, and equipment used in food preparation and sanitization of the food.

The microorganisms intended to be included within the scope of the present invention are those microorganisms, which are susceptible to QACs, and more specifically are microorganisms from the genus *Staphylococcus, Streptococcus, Campylobacter, Arcobacter, Listeria, Aeromonas, Bacillus, Salmonella*, non-toxin-producing *Escherichia*, pathogenic toxin-producing *Escherichia*, and other foodborne microorganisms which are capable of causing microbial foodborne contamination of food for human or animal consumption.

Additional intended microorganisms, which are also susceptible to QACs, are fungi, such as, *Aspergillus flavum* and *Penicillium chrysogenum*, and parasites, such as *Entamoeba histolytica*.

The present invention has an important application in the food processing industry, as well as for home and institutional food preparation. QACs are readily available and the cost of carrying out the method of the present invention is not expensive as compared to existing antimicrobial processes. Unlike existing treatments using, for example, TSP, the use of QACs does not alter the appearance, color, taste, or texture of the food product. A range of concentrations of QACs are effective in preventing broad spectrum microbial growth on food products. QACs are tested by the Ames assay for mutagenicity. The preferred QAC of the present invention, CPC, was shown to be nonmutagenic by the Ames assay. Further, CPC is already approved for human use in products for oral ingestion in preparations, such as Cepacol7 lozenges which are orally ingested in amounts up to 20 mg per day.

The present invention also is directed to an improved method of contacting food products with QAC, wherein the application time of the QAC to the food product is for at least a fraction of a second, and may be for a period of time ranging from about 0.1 second to about 5 seconds. A range of about 1 to 2 seconds may also be used. It is important that the application time of the QAC be for a sufficient time to result in significant prevention of growth of microorganisms on the food products.

The present invention also includes an improved method of contacting QACs with food products by spraying or misting the compound on the food product. The spraying or misting method can be performed using a QAC solution diluted in water or using the new concentrated formulation with QAC formulated with at least one solubility enhancing agent or the concentrated QAC formulation diluted in water. The direct spraying or misting of the concentrate may be possible if the percentage of QAC in the concentrate is approved for use on food products.

The present invention is intended to encompass any method that contacts the QAC solution with a food product by any direct means, including spraying, misting, dipping, soaking. But the present invention also is intended to include contact of the QAC solution with the food by indirect means, such as applying the QAC solution, concentrated or dilute, to equipment or food product processing or preparation surfaces in which the food product is contacted during processing, preparation, storage and/or packaging.

Further, the method of the present invention can optionally include a determination step prior to contacting the food product with the QACs to determine the presence of microorganisms on the food before treatment. Any conventional methods for rapidly determining the presence of microorganisms can be utilized as the determination step, which for example, includes PCR and immunoassays.

Additionally, the method of the present invention optionally includes a step to determine the presence of QACs on the surface of the food product after contact with the QACs. This determination is performed immediately after the contacting step or after several washing steps. For example, the QAC is extracted from the tissues of the food in a form suitable for high performance liquid chromatography (HPLC) analysis. The method comprises ethanol extraction of the food tissue followed by solid-phase extraction using a weak cationic exchange column that selectively separates QACs from other compounds in the matrix that would otherwise interfere with the HPLC analysis. The HPLC assay for quantitation of QAC residues employs a reverse phase cyano column and uses a QAC analog as an internal standard.

DETAILED DESCRIPTION OF THE INVENTION

Figure 1:
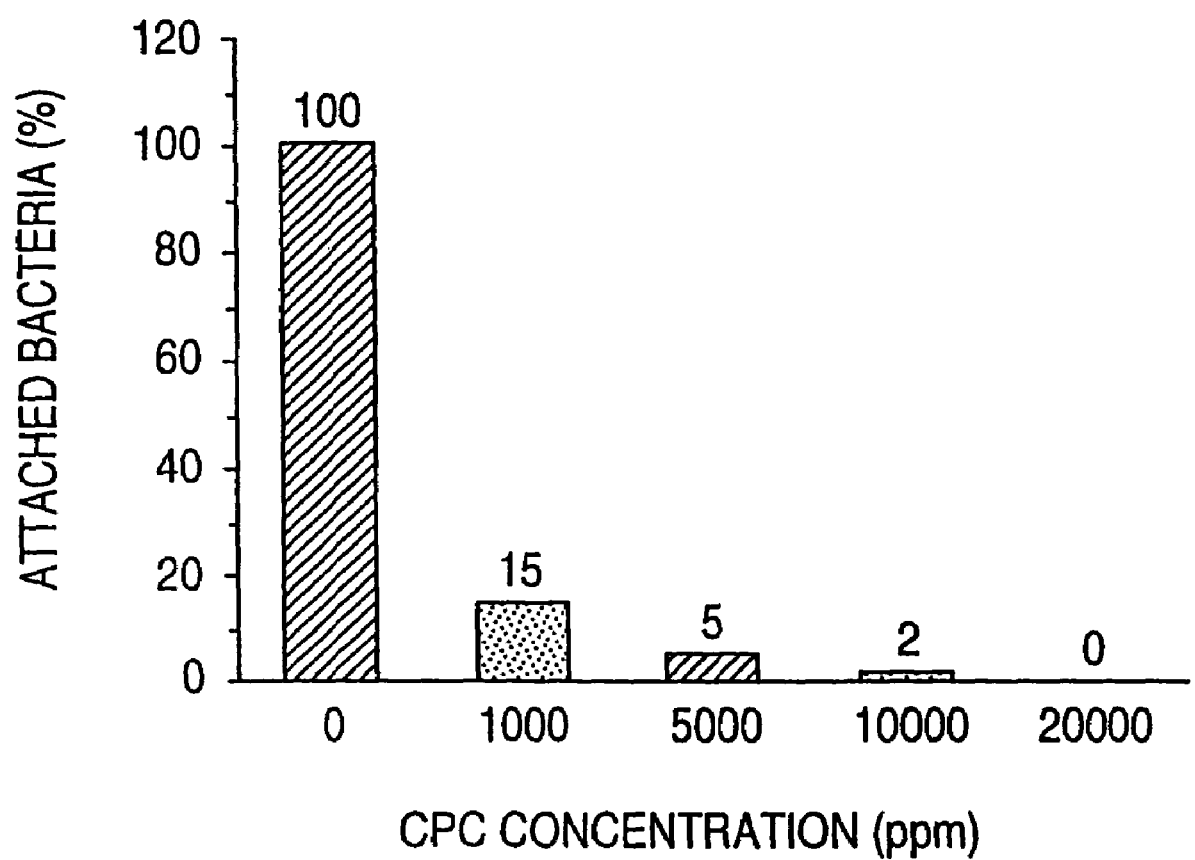
FIG. 1 is a bar graph showing the inhibition of attachment of *E. coli* O157:H7 to beef flank tissue after treatment with CPC.

The present invention is based upon the determination that QACs are useful to treat a broad range of food products to reduce a broad spectrum of foodborne microbial contamination on these food products and surfaces associated with the processing and preparation of these food products. The present invention is also based upon the finding that QACs are effective in removing, killing, inactivating and inhibiting the attachment of a broad range of foodborne pathogenic microorganisms to food products. These microorganisms include but are not limited to bacteria belonging to the genuses, *Salmonella, Staphylococcus, Streptococcus, Campylobacter, Arcobacter, Listeria, Aeromonas, Bacillus*, non-toxin-producing *Escherichia*, and the virulent toxin-producing *Escherichia* strains, such as *E. coli* O157:H7; fungi, such as *Aspergillus flavus* and *Penicillium chrysogenum*; and parasites, such as *Entamoeba histolytica*.

The compositions of the present invention comprise an effective amount of QAC in an aqueous solution. Particularly, the concentrated QAC solution of the present invention provides an ideal antimicrobial solution for use in industrial applications, where large quantities of diluted QAC solutions are needed for food processing. The concentrated solution of the present invention contains as a minimum number of components, GRAS (generally recognized as safe) components and solubility enhancing agents.

The concentrated QAC solutions of the present invention provide many advantages in the preparation of diluted QAC solutions. Large amounts of QAC powder go into solution in an aqueous solvent containing at least one solubility enhancing agent. It is difficult to prepare concentrated solutions of QACs in water alone because the QAC precipitates out of solution. In fact, it is difficult to get more than about 5 to about 10% QACs, and under some conditions more than 1% of QAC in solution, depending upon the temperature of the solution without the aid of solubility enhancing agents. However, the present inventors have determined that concentrated solutions of QACs can be prepared, if prepared in combination with at least one solubility enhancing agent or solvent, such as an alcohol or a polyglycol. QACs are known cationic surfactants, and as such, the preparation of aqueous QAC solutions results in extensive foaming. However, when the concentrated QAC solution comprising a QAC with a concentration of greater than 10% or greater than 15% and at least one solubility enhancing agent is utilized to prepare dilute QAC solutions, the extensive foaming that usually arises when preparing aqueous solutions of QAC is greatly reduced. Minimal foaming occurs in the preparation of the concentrate, and once prepared, the concentrate does not exhibit foaming. Further, the concentrate is diluted with minimal agitation and, therefore, minimal foaming. If the concentrated QAC is exposed to cold temperatures, the concentrated QAC solution resists precipitation. If frozen, the concentrated QAC solution with at least one solubility enhancing agent goes into solution upon thawing. If a precipitate of the QAC remains after shipping or storage at ambient temperatures or frozen, then the temperature of the solution is raised until the precipitate disappears. Large quantities of QAC concentrates in large containers or drums can be warmed on a drum warmer, if necessary. Further, compared to dilute aqueous solutions of QACs, the concentrated QAC solution, in conjunction with the high concentrations of at least one solubility enhancing agent, such as appropriate water-miscible organic solvents, have a minimal risk of spoilage or limited shelf life. Additionally, the concentrated QAC solutions enhance end-user safety by eliminating inhalation exposure to QAC dust, which is a problem during the handling of QAC powder, particularly when handled in large quantities because it can cause lung, eye, throat, nasal and skin irritation. The concentrated QAC solution decreases the volume and mass of solution to be transported and warehoused during industrial applications of QAC solutions. And most importantly, when the concentrated QAC solution is diluted in water to prepare dilute QAC solutions for application to food products, the diluted concentrate solution demonstrates very good antimicrobial efficacy.

The present invention is particularly directed to a concentrated QAC solution comprising a quaternary ammonium compound with a concentration from greater than about 10% by weight and at least one solubility enhancing agent. The solubility enhancing agent is any water-miscible organic solvent that enhances the solubility of the QAC powder in an aqueous solution so that it forms a solution at concentrations of greater than 10% by weight. A 10% by weight solution is made by weighing 10 grams of QAC and dissolving it in 90 grams of liquid that comprises at least one solubility enhancing agent and water, if water is necessary to bring the weight to 90 grams of liquid. The concentrated QAC solution of the present invention comprises QAC in solution at concentrations of greater than about 10% by weight, and more preferably at concentrations of greater than about 15% by weight. The concentrated QAC solution comprises QAC in solution at concentrations ranging from greater than about 10% or greater than about 15% by weight to about 60% by weight. Although a greater than about 60% by weight concentration of QAC can be used in the concentrated QAC solution, the upper limit that is useful is governed by the interaction between the % (or weight) of QAC and the solubility enhancing agent(s) used to prepare the concentrated solution. Specific solubility enhancing agents or combinations of these agents may result in higher than 60% QAC concentrated formulations. It is important to dissolve all of the QAC powder and get it into solution prior to preparing the dilute formulation to treat food products. Preferably, the QAC is present at a concentration from greater than about 10% or greater than about 15% by weight to about 50% by weight, and more preferably at a concentration from greater than about 10% or about 15% by weight to about 40% by weight. But the concentration of the QAC in the range of greater than about 10% to about 30% by weight or between about 15% to about 25% by weight and within this range about 20% by weight is also useful in the present concentrate solution.

The QAC concentrations in the present invention are described by concentrations as either parts per million (ppm) or % by weight, where 100,000 ppm is equal to 10% by weight. The examples utilize CPC and use both ppm or % to designate concentration.

The solubility enhancing agent or a combination of these agents, and water if necessary, to make up the remaining weight of the solution, is added to reach 100% by weight. The solubility enhancing agent is any compatible solubility enhancing agent that solubilizes QACs at concentrations of greater than about 10% by weight is contemplated by the present invention, but alcohols are the preferred solubility enhancing agent. Additionally polyglycols are useful solubility enhancing agents, such as polyethylene glycol. The present invention contemplates using one or more of these solubility enhancing agents. More preferably, the alcohol is selected from the group consisting of a monohydric alcohol, a dihydric alcohol, a trihydric alcohol, and a combination thereof. Any one of these types of alcohols can be used alone or in combination with one or more of the other types of alcohols to obtain the desired % by weight of the solubility enhancing agent. If a monohydric alcohol is utilized, then this type of alcohol is preferably an aliphatic alcohol, and more preferably is ethyl alcohol. If a dihydric alcohol is utilized, then a glycol or a derivative thereof, is preferred. Of the glycols, propylene glycol is most preferred and is available from any number of suppliers. Propylene glycol provides advantages over other alcohols, as a solubility enhancing agent of high concentrations of QACs, such as CPC. Trihydric alcohols, such as glycerol or derivatives thereof, are also useful as a solubility enhancing agent in the present concentrated CPC solution. The choice of the alcohol depends upon the food product that is contacted and is selected to be compatible with treatment steps prior to or after the QAC contact with the food product. If a polyglycol is used as the solubility enhancing agent, then polyethylene glycol is preferred, and particularly the lower molecular weight species with an average molecular weight of less than or equal to 600, are well known and possess properties similar to propylene glycol.

If ethyl alcohol is used as the solubility enhancing agent, it is present at a concentration up to about 49% by weight. Ranges of ethyl alcohol about 0.5% weight to about 49% by weight, from about 10% by weight to about 40% by weight, from about 15% by weight to about 30% by weight, and within the range at about 20% is useful in the present invention.

The concentrated QAC solution contains at least one solubility enhancing agent, such as an alcohol at a concentration of up to about 70% by weight. More preferably, the alcohol is present at a concentration of up to about 60% by weight, and may range from about 10% by weight to about 60% by weight. The concentration of the solubility enhancing agent varies depending on the % weight of the QAC, which is to be dissolved in solution, as well as the particular intended use of the concentrated QAC solution and dilutions thereof.

Preferably the concentrated QAC solution comprises a QAC at a concentration of about 40% by weight and at least one alcohol at a concentration ranging from between about 50% by weight to about 60% by weight with water making up the remaining % weight. The preferred alcohol in this solution is propylene glycol. More preferably, the concentrated QAC solution comprises a QAC at a concentration of about 40% by weight and at least one alcohol at a concentration ranging between about 55% by weight to about 60% by weight and water present at about 5% by weight. The most preferred concentrated QAC solution comprises a QAC at a concentration of about 40% by weight, an alcohol at a concentration of about 57% by weight and water present at about 3% by weight. Again, the preferred alcohol in this solution is propylene glycol.

However, also useful is a concentrated QAC solution comprising a QAC at a concentration of about 40% by weight and at least one alcohol at a concentration of up to about 50% by weight, and preferably about 50% by weight. In this concentrated aqueous solution, the solubility enhancing agent may be a combination of alcohols, such as ethyl alcohol and propylene glycol. But glycerol also is useful as the solubility enhancing agent, alone or in combination with other alcohols or polyglycols. Glycerol is useful for this purpose at a concentration of up to and including about 20% by weight, and also is useful at concentrations ranging from about 0.5% to about 10% by weight, and within this range at about 1%. Glycerol is useful in methods where propylene glycol is not the alcohol of choice for solubilizing the QAC. A further useful concentrated QAC solution comprises a QAC at a concentration of about 20% by weight and at least one alcohol at a concentration of about 50% by weight, such as a combination of ethyl alcohol and propylene glycol, and preferably where each alcohol is present at about 25% by weight.

The QAC useful in the present concentrated QAC solution is selected from the group consisting of alkylpyridinium, tetra-alkylammonium and alkylalicyclic ammonium salts.

Alkylpyridinium is represented by the structural formula (I):

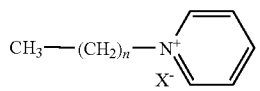

wherein n is 9-21; and X is a halide.

Tetra-alkylammonium is represented by the structural formula (II):

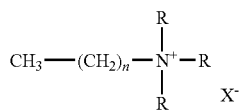

wherein n is 9-21; R is selected from the group consisting of $CH_3$ and $C_2H_5$; and X is a halide.

Alkylalicyclic ammonium salts are represented by the structural formula (III):

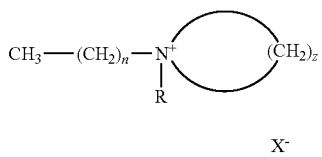

wherein n is 9-21; Z is 4-5; R is selected from the group consisting of $CH_3$ and $C_2H_5$; and X is a halide.

A variety of QACs, all of which are cationic surface-active agents; i.e., surfactants, are evaluated for their effectiveness in removing attached microorganisms from various foods as well as in inhibiting the attachment of the microorganisms. Of the QACs studied, cetylpyridinium chloride (CPC) was the most effective and is utilized in the examples set forth below but it not intended to limit the use of QACs to CPC within the meaning of the present invention because other members of QACs also have similar properties against the foodborne pathogenic microorganisms. QACs containing between 12 to 16 carbons on the long side chain possess maximum antimicrobial activity. CPC, the preferred QAC, contains 16 carbons in the long side chain.

The present invention further involves the dilution of the concentrated QAC solution, including at least solubility enhancing agent, and water, if required to obtain the desired % by weight of CPC, and the contacting of this diluted QAC solution with a food product to prevent microbial growth or attachment on the food product. The diluted QAC solution comprises QAC at a concentration of up to and including about 1% QAC by weight. This % by weight is the current acceptable concentration of QAC under consideration to treat food products by the United States Department of Agriculture. The amount of QAC that remains on a particular food product varies with the different types of foods treated and the method of application. The concentrated QAC solution described in the present invention is diluted with water to obtain a dilute solution with the QAC ranging from about 0.01% up to and including about 1% but may be increased or decreased depending upon the food product treated and the application method used. The concentrated QAC solution, that was prepared on a weight to weight basis as described previously, is diluted to obtain the desired treatment QAC concentration by a volume to volume dilution. For example, a 40% concentrated QAC solution is diluted to 1% QAC by diluting 2.5 milliliters of the QAC concentrate with 97.5 millilters of water. In a food processing plant, this volume to volume dilution is preferred because it is easy to prepare. However, a weight to weight dilution also may be used to prepare dilute QAC solutions, in which 2.5 grams of a 40% by weight QAC solution is mixed with 97.5 grams of water to obtain a 1% QAC solution. The dilution of the QAC in the concentrated solution also results in the dilution of the solubility enhancing agent that is in the concentrated solution. The diluted QAC concentrate solution is useful for contacting the food product by spraying, misting, immersion, and any other contact method that is suitable for contact of the dilute QAC solution with the food product, including indirect contact, such as contacting equipment or food product processing or preparation surfaces that are contacted with the food during processing, preparation, storage and/or packaging. The shorter the application time of the QAC solution, the better, particularly for industrial and commercial food processing purposes.

The present invention is further based on the determination that the application time of the QACs with the food product in the spraying or misting process can be reduced to as low as about at least 0.1 second while still resulting in significant inhibition of microorganism attachment, for foodborne microorganisms, which is a significant improvement and a commercial advantage in the industrial use of this process. The misting or spraying application process allows an application time of the dilute QAC solution with the food product for as short a time as up to 20 seconds, but more preferably for about 10 seconds or less, and more preferably for about 5 seconds or less. The most preferred range of application time of the QAC on the food product is from about 0.1 second to about 5 seconds, and within that range, from about 0.1 to about 2 seconds also is useful, with a preferred range of about 0.5 second to about 2 seconds. It should be understood that the present invention contemplates as short an application time of the dilute QAC solution as is physically possible, while still resulting in inhibition of microorganisms on the food products or in the liquid and surfaces in which the food product contacts. Therefore, different intervals of time less than 20 seconds are contemplated by the present invention.

Any type of method of contact of the QAC with the food product is useful in the present method as long as it is capable of allowing a short application time. A method that utilizes a cabinet that provides spraying or misting of the food product is useful in the present invention. Machinery for use in such cabinets on a processing line in a food processing plant are adaptable for reducing the application time to a minimum while still obtaining efficacious antimicrobial effects on the food. All of these short application times; i.e., less than 20 seconds, and as low as 0.1 second, significantly reduce the viable foodborne microorganisms on these food products. Additionally, a very small amount of QAC diluted solution is necessary for the spraying or misting treatment, for example, as little as about 1 ounce of diluted QAC solution per pound of food product is useful for efficacious treatment.

The present method of short QAC application time in a poultry processing plant is useful for treating post-chilled chickens, that have been immersed in a chill bath of cold water. The chickens are removed from the chill bath and treated with the diluted QAC solution of the present invention for an application time of less than about 20 seconds, preferably less than about 10 seconds, more preferably less than about 5 seconds, most preferably less than about 2 seconds, and even as short as 0.1 second. The treated chickens are subsequently packaged without further washing or rinsing. However, the method optionally may include, if deemed necessary, at least one washing step of the chickens prior to packaging. The optional washing step may include spraying or misting the food product with water or immersing the food product in a container or tank of water.

The above described aspects of the present invention are described in detail below with in certain examples with reference to FIGS. 1-5.

The examples set forth below serve to further illustrate the present invention in its preferred embodiments, and are not intended to limit the present invention. The examples utilize poultry, beef, catfish, broccoli, and grapes as the food products treated in the method, but it is intended that the treatment of other food products, which would not be adversely affected by the treatment process are also intended to be encompassed by the present invention.

EXAMPLES

The microorganisms utilized in the following examples are as follows: *Staphylococcus aureus* ATCC 29213, *Campylobacter jejuni* ATTC 29428, *Escherichia coli* (non-toxin producing strain) ATCC 25922; *Escherichia coli* O157:H7 (toxin-producing strain) ATCC 43895, *Arcobacter butzleri* ATCC 49616, *Listeria monocytogenes* ATCC 49594, *Aeromonas hydrophila* ATCC 49140, *Bacillus cereus* ATCC 49063, *Salmonella typhimurium* ATCC 14028 and NCTC 12023, and commercially available cultures of *Aspergillus flavus* and *Penicillium chrysogenum*.

Example 1

Bactericidal Activity of Quaternary Ammonium Compounds in Suspension Cultures (Not Attached to Meat Products)

Minimum Inhibitory Concentration (MIC) of Quaternary Ammonium Compounds

Minimum inhibitory concentrations (MIC) for QAC were determined in Mueller Hinton broth (BBL Microbiology System) using the macrodilution method established by the 1987 National Committee for Clinical Laboratory Standards. Experiments were conducted by 16 hour incubation at 37° C. for *Staphylococcus aureus*, *Escherichia coli* O157:H7, *Listeria monocytogenes*, and *Salmonella typhimurium*. For *Aeromonas hydrophila*, and *Bacillus cereus* incubations were performed at 30° C. MIC were determined by the lowest dilution with no visible turbidity. Table 2 shows the data from the above experiment:

TABLE 2

MINIMAL INHIBITORY CONCENTRATION (MIC)

| Cetylpyridinium chloride, (CPC) µg/mL | CPC vs E. coli O157:H7 | CPC Vs B. cereus | CPC Vs S. aureus | CPC Vs S. typhimurium | CPC Vs A. hydrophila | CPC vs L. monocytogenes |
|---|---|---|---|---|---|---|
| 125 | − | − | − | − | − | − |
| 62.5 | − | − | − | − | − | − |
| 31.25 | − | − | − | + | + | − |
| 15.63 | − | − | − | + | + | − |
| 7.81 | + | − | − | + | + | − |
| 3.91 | + | + | − | + | + | − |
| 1.96 | + | + | − | + | + | − |
| 0.98 | + | + | − | + | + | − |
| 0.50 | + | + | − | + | + | + |
| 0.25 | + | + | − | + | + | + |
| 0.00 | + | + | + | + | + | + |

(−) No growth
(+) Growth
MICs were obtained by the macrodilution broth method (National Committee for Clinical Laboratory Standards).

Minimum Bactericidal Concentration (MIC) of Quaternary Ammonium Compounds

Minimum bactericidal concentrations (MBC) for QAC towards *Campylobacter jejuni* and *Arcobacter butzleri* were determined in Mueller Hinton broth (BBL Microbiology System) using the macrodilution method established by the 1987 National Committee for Clinical Laboratory Standards. Experiments were conducted by microaerophilic incubation at 37° C. for 48 hours. An aliquot of each dilution was pour plated in agar and incubated in microaerophilic conditions at 37° C. for 48 hours. MBCs were determined as the lowest dilution with no growth. Table 3 shows the data from the above experiment:

TABLE 3

MINIMAL BACTERICIDAL CONCENTRATION (MBC)

| Cetylpyridinium Chloride, µg/mL | CPC Vs Campylobacter Jejuni | CPC Vs Arcobacter Butzleri |
|---|---|---|
| 125 | − | − |
| 62.5 | − | − |
| 31.25 | − | + |
| 15.63 | − | + |
| 7.81 | − | + |
| 3.91 | + | + |
| 1.96 | + | + |
| 0.98 | + | + |
| 0.50 | + | + |

TABLE 3-continued

MINIMAL BACTERICIDAL CONCENTRATION (MBC)

| Cetylpyridinium Chloride, µg/mL | CPC Vs Campylobacter Jejuni | CPC Vs Arcobacter Butzleri |
|---|---|---|
| 0.25 | + | + |
| 0.00 | + | + |

(−) No growth
(+) Growth
MBCs were obtained by the macrodilution broth method (National Committee for Clinical Laboratory Standards).

The MIC and MBC data shows that CPC is effective against a broad range of microorganisms.

Activity of Quaternary Ammonium Compounds in Planktonic Cells

A 16-hour culture of each of *E. coli* O157:H7 in trypticase soy broth was centrifuged (15,000 rpm, 10 min, 4° C.). After removal of the supernatant, the pellet was washed with 10 ml 0.04M potassium phosphate buffer (PPB, pH 7.0), and suspended in PPB to a final suspension of $1-2\times10^9$ cells/ml. Aliquots (1.0 ml) were centrifuged (14,000 rpm, 3 min), and the supernatants were removed. Each pellet was suspended in either 1 ml of an aqueous solution of various concentrations (100-1,000 µg/ml) of test composition (CPC) or 1.0 ml of PPB, vortexed (30 sec), incubated for 1 min at 25° C., and centrifuged (14,000 rpm, 3 min). After removal of the supernatant, each pellet was suspended in 0.5 ml PPB. Cells from each sample were counted using duplicate 0.05 ml aliquots and standard serial dilution techniques on trypticase soy agar, and the data recorded as mean colony-forming units (CFU)/ml.

The results of the above experiment show complete reduction of viable *E. coli* O157:H7 in suspension was achieved at all concentrations of CPC tested (100, 250, 500, and 1000 µg/ml). The results of this experiment are particularly significant for the prevention of cross contamination with *E. coli* O157:H7 in industrial processing of meat. As discussed above, this strain of toxin-producing *E. coli* shows resistance to many broad spectrum antimicrobial agents. These results provide evidence that treatment of meat products with QAC will prevent one contaminated piece of meat from contaminating other uncontaminated pieces because the QAC will kill the organism in the liquid which is the transfer agent responsible for the cross contamination.

Example 2

Effects of Quaternary Ammonium Compounds on the Reduction of Viable Bacteria Attached to Chicken Skin Chicken skins (2.5×2.5 cm) excised from a drumstick, sterilized by a 45 KGy dose of irradiation from an electron source, were placed epidermal side up in each well of six-well tissue culture plate. Each skin piece was inoculated with 5 ml 0.008 M phosphate buffered saline (PBS, pH 7.2) containing $6-8\times10^3$ CFU/ml bacteria with the exception of the background control group that was treated only with 5 ml of PBS. The plates were incubated (30 min, 35° C.), and each skin piece was rinsed (2×, 5 ml PBS) to remove loosely bound (unattached) microorganisms. Each inoculated skin was treated with 5 ml of PBS containing CPC. Three pieces of skin were used for each concentration of CPC, including one in which the skins were treated only with 5 ml of PBS (0 concentration). The plates were incubated with shaking (100 rpm) for 30 min at 25° C. After incubation, each skin piece was rinsed (5 ml PBS), placed in a sterile plastic bag containing 80 ml of saline or 1% peptone, and homogenized for 2 minutes using a laboratory blender (Stomacher7 400, Seward Medical, London, England). Three aliquots of the homogenate (1 ml) were pour-plated and incubated (37° C., 18-24 hr). Bacterial colonies were counted, corrected for dilution, and reported as CFU/skin.

These studies show the reduction in viable bacteria (*Salmonella typhimurium, Staphylococcus aureus, Campylobacter jejuni, Escherichia coli* (non-toxin producing strain) and *Escherichia coli* O157:H7) after treatment with 50 to 1000 ppm concentrations of CPC. Higher concentrations of CPC up to 8,000 ppm were tested against *Escherichia coli* O157:H7 and found to reduce the number of attached bacteria to below 0.1%. These studies show significant inhibition of the growth of these five bacteria on chicken skin.

Example 3

Effects of Quaternary Ammonium Compounds on the Inhibition of Bacterial Attachment to Chicken Skin Chicken skins (2.5×2.5 cm) excised from a drumstick, sterilized by a 45 KGy dose of irradiation from an electron source, were placed epidermal side up in each well of six-well tissue culture plate. Each skin piece was inoculated with 5 ml 0.008 M phosphate buffered saline (PBS, pH 7.2) containing CPC. Three pieces of skin were used for each concentration of test compound, including one in which the skins were treated only with 5 ml of PBS (0 concentration). The plates were incubated with shaking (100 rpm) for various times (1 min or 10 min) at 25° C. The incubating solution was removed by aspiration, and the skins were rinsed (5 ml PBS), and then incubated 30 min, 35° C. with 5 ml of PBS containing $6-8\times10^3$ CFU/ml bacteria. After incubation, each skin piece was rinsed (2×, 5 ml PBS), to remove loosely bound (unattached) microorganisms, placed in a sterile plastic bag containing 80 ml of saline or 1% peptone, and homogenized for 2 minutes using a laboratory blender (Stomacher7 400, Seward Medical, London, England). Three aliquots of the homogenate (1 ml) were pour-plated and incubated (37° C., 18-24 hr). Bacterial colonies were counted, corrected for dilution, and reported as CFU/skin.

These studies show the inhibition of attachment of bacteria (*Salmonella typhimurium, Staphylococcus aureus, Campylobacter jejuni, Escherichia coli* (non-toxin producing strain) and *Escherichia coli* O157:H7) to chicken skin after treatment with 50 to 1000 ppm concentrations of CPC. The data in these studies show that pretreating chicken skin with CPC significantly inhibits the attachment of these microorganisms to the chicken skin.

Treating chicken skin with CPC for only 1 minute results in significant inhibition of attachment of *S. typhimurium* at 500 ppm and 1000 ppm. This shorter contact time of QAC with the meat products supports using shorter contact times than have been previously reported as being effective. Generally, chill tank immersions can for up to 60 minutes but the data presented herein supports that a shorter contact or immersion time can be used which still results in significant reduction in the number of viable microorganisms. The CPC contacting step of the present invention can be performed for approximately 20 seconds to about 60 minutes. The present invention also discloses useful contact times within this range of less than 10 minutes, and at ranges of about 20 seconds to about 9 minutes, of about 20 seconds to about 5 minutes, and of about 20 seconds to about 90 seconds.

Example 4

Effects of Quaternary Ammonium Compounds on the Reduction of Viable Bacteria Attached to Beef Flank Steak Beef flank tissue squares (2.5×2.5 cm) approximately 0.5 cm thick, sterilized by a 45 KGy dose of irradiation from an electron source, were placed in each well of six-well tissue culture plate. Each tissue piece was inoculated with 5 ml 0.008 M phosphate buffered saline (PBS, pH 7.2) containing $6\text{-}8\times10^3$ CFU/ml bacteria with the exception of the background control group that was treated only with 5 ml of PBS. The plates were incubated (30 min, 35° C.), and each square was rinsed (2×, 5 ml PBS) to remove loosely bound (unattached) microorganisms. The inoculated squares were treated with 5 ml of PBS containing the CPC. Three pieces of tissue were used for each concentration of test compound, including one in which the squares were treated only with 5 ml of PBS (0 concentration). The plates were incubated with shaking (100 rpm) for 30 min at 25° C. After incubation, each square was rinsed (5 ml PBS), placed in a sterile plastic bag containing 50 ml of 1% peptone, and homogenized for 2 minutes using a laboratory blender (Stomacher7 400, Seward Medical, London, England). Three aliquots of the homogenate (1 ml) were pour-plated and incubated (37° C., 18-24 hr). Bacterial colonies were counted, corrected for dilution, and reported as CFU/square.

The results of this study show a reduction in viable *Escherichia coli* O157:H7 after treatment with 50 to 1000 ppm concentrations of CPC on beef flank tissue with 62-64% reduction in attached bacteria at 500 and 1000 ppm CPC.

Example 5

Effects of Quaternary Ammonium Compounds on the Inhibition of Bacterial Attachment to Beef Flank Tissue Beef flank tissue squares (2.5×2.5 cm), approximately 0.5 cm thick, sterilized by a 45 KGy dose of irradiation from an electron source, were placed in each well of six-well tissue culture plate. Each tissue piece was treated with 5 ml 0.008 M phosphate buffered saline (PBS, pH 7.2) containing CPC. Three pieces of beef tissue were used for each concentration of test compound, including one in which the squares were treated only with 5 ml of PBS (0 concentration). The culture plates were incubated with shaking (100 rpm) for 10 minutes at 25° C. The incubating solution was removed by aspiration, and the squares were rinsed (5 ml PBS), and then incubated (30 min, 35° C.) with 5 ml of PBS containing $6\text{-}8\times10^3$ CFU/ml bacteria. After incubation, each tissue piece was rinsed (2×, 5 ml PBS), to remove loosely bound (unattached) microorganisms, placed in a sterile plastic bag containing 50 ml of 1% peptone, and homogenized for 2 minutes using a laboratory blender (Stomacher7 400, Seward Medical, London, England). Three aliquots of the homogenate (1 ml) were pour-plated and incubated (37° C., 18-24 hr). Bacterial colonies were counted, corrected for dilution, and reported as CFU/square.

The results of this study show the inhibition of attachment of *Escherichia coli* O157:H7 after treatment with 50 to 1000 ppm of CPC with a 76% reduction in the number of bacteria attached to the beef at concentrations of 1000 ppm CPC. FIG. 1 shows the results of a separate trial using higher concentrations of CPC and the same experimental procedure. At 20,000 ppm CPC, the bacteria was completely inhibited from attaching to beef.

Example 6

Pre-Chill Poultry Spraying with 0.1% Cetylpyridinium Chloride

A spraying test chamber was designed and constructed for use in a poultry processing pilot plant. The spraying test system consisted of a testing chamber, a spraying water storage tank, a pressure pump, a filter, pressure regulators, a plastic spraying chamber with eight nozzles located on four sides, and a used water collector. There were three nozzles on each of the pipes for front and back spraying. One nozzle was used for top spraying and one nozzle for bottom spraying. The chamber dimensions preferably are 3×3×3 feet. With a high pressure booster pump, the pressure could be adjusted between 0-140 psi. The distance between the spraying nozzles and the chicken carcass was 12-15 inches. The top nozzle was used to spray the inside of the chicken carcass. Flat-cone spraying nozzles (⅛TK-SS1, Spraying Systems Co.) were used.

The spray solution in the storage tank was pumped to the pressure regulator, and then sprayed through the nozzles in the chamber. In the spraying chamber, several spraying layers consisting of stainless steel nozzles and pipes were installed, and the chamber was covered with plastic sheets to prevent chemical drift. A shackle was used to hang up a chicken carcass in the chamber.

Pre-chill chicken carcasses were obtained from a local poultry processing plant. They were taken from the end of an evisceration processing line, transported to the research laboratory, and immediately used for the tests. The time elapsed between the processing plant and the research laboratory was less than one half hour. The temperature of chicken carcasses was in the range of 32-37° C.

Chicken carcasses were inoculated by spraying 1 ml of *S. typhimurium* at $1\times10^6$ CFU/ml and then incubated at room temperature for 30 min. The inoculated chicken carcasses were rinsed by spraying tap water at 30 psi and 22° C. for 5 sec. to wash off loosely attached *Salmonella* cells. Then each carcass was hung in the spraying chamber and sprayed with one of the test compounds. After spraying, each chicken carcass was rinsed with tap water for 20 sec. The chicken carcasses were then washed with buffered peptone water in a plastic bag on an automatic shaker to get samples for microbial analysis. The color of chicken skin was examined visually by comparing the birds treated with test compounds, such as QACs, with untreated birds.

CPC at a concentration of 1000 ppm was used at different spraying pressures and durations. Spraying water temperature was set at room temperature of 22° C. Pressures were set at 30, 50, and 120 psi, and duration at 30 and 90 sec. Three replicates were performed for each trial. Reduction of *S. typhimurium* on chicken carcasses was compared among test compound sprayed, water sprayed, and non-sprayed groups.

After spraying treatments, each carcass was mechanically shaken with 100 ml of buffered peptone water (BPW) for 1 min, and then the wash water was collected. The samples were diluted, enriched, plated on XLT agar or Petrifilm (3M, Inc.; St. Paul, Minn. for total aerobic count plates) and incubated for 18-24 hours at 37° C. Then, colony forming units were counted. The number of attached bacteria was calculated using a most-probable-number technique. The most probable numbers of *Salmonella* and total aerobic plate counts were performed for each carcass using the wash water samples. An analysis of variance was used to analyze the experimental data to determine any significant differences among the treatment groups and controls (SAS/STAT User's Guide, SAS Institute, Inc., Cary, N.C. 1993).

The results of this experiment show that 30 and 90 second spraying of 1000 ppm solution of CPC at pressures of 30, 50, and 120 psi cause a significant reduction in the number of *Salmonella* on chicken carcasses. This data shows that the spraying method is a viable alternate method to the standard method of immersion or dipping of chickens when sprayed for 30 seconds to 90 seconds with a pressure in the range of 30 to 120 psi at 0.1% CPC concentration. It may be possible to use lower concentrations of CPC with varying spray pressures within the disclosed range of 30 to 120 or greater psi and varying spray times to obtain the most efficient process which results in significant reduction in the foodborne microorganisms. The spraying method would be advantageous to use in industrial processes because many chicken carcasses could be sprayed automatically for short periods of time and yet result in significant reduction of pathogenic bacteria.

Example 7

Effective Concentration and Time Study of the Effects of Quaternary Ammonium Compounds on *S. Typhimurium* on Chicken Skin The effects of CPC on the inhibition and reduction of viable *S. typhimurium* on chicken skin were studied. Test solutions comprised various concentrations of CPC (Sigma Chemical Co., St. Louis, Mo.) in 5% (v/v) glycerin in 0.008 M, pH 7.2 phosphate buffered saline (PBS). The solutions were prepared by dissolving the appropriate amounts of CPC in the glycerin-PBS mixture. Skin squares (2.5×2.5 cm) from drumsticks of freshly frozen, unprocessed chickens were sterilized by a 45 kGy dose of irradiation (electron beam from a linear accelerator, Iowa State University). The source of *S. typhimurium* was ATCC strain # 14028 or NCTC strain # 12023). All colony counts were performed on tryptic soy agar (TSA; DIFCO, Detroit, Mich.) plates. *Salmonella* storage was on TSA. Inoculum preparation was performed as follows. A flask containing 50 ml tryptic soy broth was inoculated with *S. typhimurium* from a single colony and then incubated (37° C.) with shaking (150 rpm) overnight. A one ml aliquot of the culture was washed with 9 ml PBS (4800 rpm, 10 min.) two times. The pellet was resuspended in PBS to obtain a final cell concentration (spectrophotometrically, 420 nm) of 1 to 2×10$^6$ colony forming units (CFU) per ml.

Chicken skin was excised from drumsticks and placed epidermal side up in each well of six-well tissue culture plates. Skin pieces were inoculated with 5 ml of PBS containing 1 to 2×10$^6$ CFU of *S. typhimurium* per ml, with the exception of the background control group that was treated only with 5 ml of PBS. Culture plates with the skin pieces were incubated (30 min., 35° C.), and then the incubating solution was removed by aspiration. The inoculated skins were treated with 5 ml of the test solution. Sets of three pieces of skin were used for each concentration of test solution, including one set in which the skins were treated only with 5 ml of 5% (v/v) glycerin in PBS (0 concentration). The plates were incubated at 25° C. with shaking (100 rpm) for 1, 3, or 10 min. After incubation, each skin piece was rinsed with aspiration (5 ml PBS), placed in a sterile plastic bag containing 50 ml of 0.1% (w/v) peptone, and homogenized for 2 minutes using a Stomacher7 400 laboratory blender (Seward Medical Co., London, England). A corner of the bag was aseptically cut and the entire contents were transferred to a sterile centrifuge tube, which was then spun for 10 min (12,000 rpm, 20° C.). The pellet was resuspended in 5 ml 0.1% (w/v) peptone/water. One ml of the appropriate dilution was pour plated onto TSA agar in triplicate and then incubated at 37° C. for 24 hour, after which colonies were counted, corrected for dilution, and reported as CFU/skin. The results show that *Salmonella* reduction was dependent upon both CPC concentration and time of exposure. Nearly a 5 $\log_{10}$ decontamination was achieved by treating with CPC solutions of 4000 and 8000 ppm for contact times as low as 3 min.

Skin squares were placed epidermal side up in each well of six-well tissue culture plates. Skin pieces were treated with 5 ml of the test solution. Sets of three pieces of skin were used for each concentration of test solution, including one set in which the skins were treated only with 5 ml of 5% (v/v) glycerin in PBS (0 concentration). Culture plates with the skin pieces were incubated at 25° C. with shaking (100 rpm) for 1, 3, or 10 min. The incubating solution was removed by aspiration, and the skins were rinsed (5 ml PBS) and then incubated (30 min., 35° C.) with 5 ml of PBS containing 1 to 2×10$^6$ CFU of *S. typhimurium* per ml. After incubation, each skin piece was rinsed with aspiration (5 ml PBS), placed in a sterile plastic bag containing 50 ml of 0.1% (w/v) peptone, and homogenized for 2 minutes using a Stomacher7 400 laboratory blender. Three aliquots of the homogenates (1 ml) were pour-plated onto TSA agar and incubated at 37° C. for 24 h and then colonies were counted, corrected for dilution, and reported as $\log_{10}$ CFU/skin. The results indicate that prevention of *Salmonella* contamination by pretreatment with CPC also showed concentration and time dependency. The most marked effects were observed for 10 minute pretreatment times where a 4.9 $\log_{10}$ inhibition of *Salmonella* attachment was shown at a concentration of 8,000 ppm. This result is important since prevention of cross-contamination is of paramount importance in food processing.

Values of $\log_{10}$ CFU/skin for controls were within the range 4.61 to 5.03. Differences between treated samples and controls were analyzed using ANOVA followed by Newman-Keuls multiple range analysis and were statistically significant ($p<0.01$).

In another spraying experiment, a 3.3 $\log_{10}$ reduction of *Salmonella* was obtained after a 90 second spraying of chicken carcasses with a 5,000 ppm solution of CPC.

Example 8

Effects of Quaternary Ammonium Compounds on the Reduction of Viable *Listeria monocytogenes* Attached to Chicken Skin The steps of Example 2 were followed except that *L. monocytogenes* was used to inoculate the chicken skin and the media in the plastic bag used in the Stomacher 400 contained 0.1% peptone. At concentrations of CPC of 2000 ppm or higher, there was greater than a 4 $\log_{10}$ reduction in *L. monocytogenes*.

Example 9

Effects of Quaternary Ammonium Compounds on the Inhibition of Attachment of Viable *Listeria monocytogenes* Attached to Chicken Skin The steps of Example 3 were followed except that *L. monocytogenes* was used to inoculate the chicken skin and the media in the plastic bag used in the Stomacher 400 contained 0.1% peptone. The results of this study show a reduction of 82% of attached bacteria at 50 ppm, reduction of 92% at 100 ppm, and reduction of 100% at 500 and 1000 ppm.

Example 10

Effects of Quaternary Ammonium Compounds on the Reduction of Viable *Salmonella typhimurium* Attached to Catfish, Black Grapes, and Broccoli The effects of CPC on the reduction of viable *S. typhimurium* on catfish, black grapes, and broccoli were studied. Test solutions comprised various concentrations of CPC (Sigma Chemical Co., St. Louis, Mo.) in 5% (v/v) glycerin in 0.008 M, pH 7.2 phosphate buffered saline (PBS). The solutions were prepared by dissolving the appropriate amounts of CPC in the glycerin-PBS mixture.

Food samples were small intact black grapes, broccoli florets, and catfish skin squares (2.5×2.5 cm) excised from unprocessed, freshly thawed catfish. The fruit and vegetables were purchased from a local grocery, while the fish was shipped frozen from a local catfish supplier. The source of *S. typhimurium* was ATCC strain # 14028 or NCTC strain # 12023).

All colony counts were performed using *Salmonella*-selective XLD agar (DIFCO, Detroit, Mich.) plates. Additionally, in the catfish experiments, total aerobic colony counts were performed using a non-selective medium, tryptic soy agar (TSA:DIFCO, Detroit, Mich.). *Salmonella* storage was on TSA.

Figure 2:
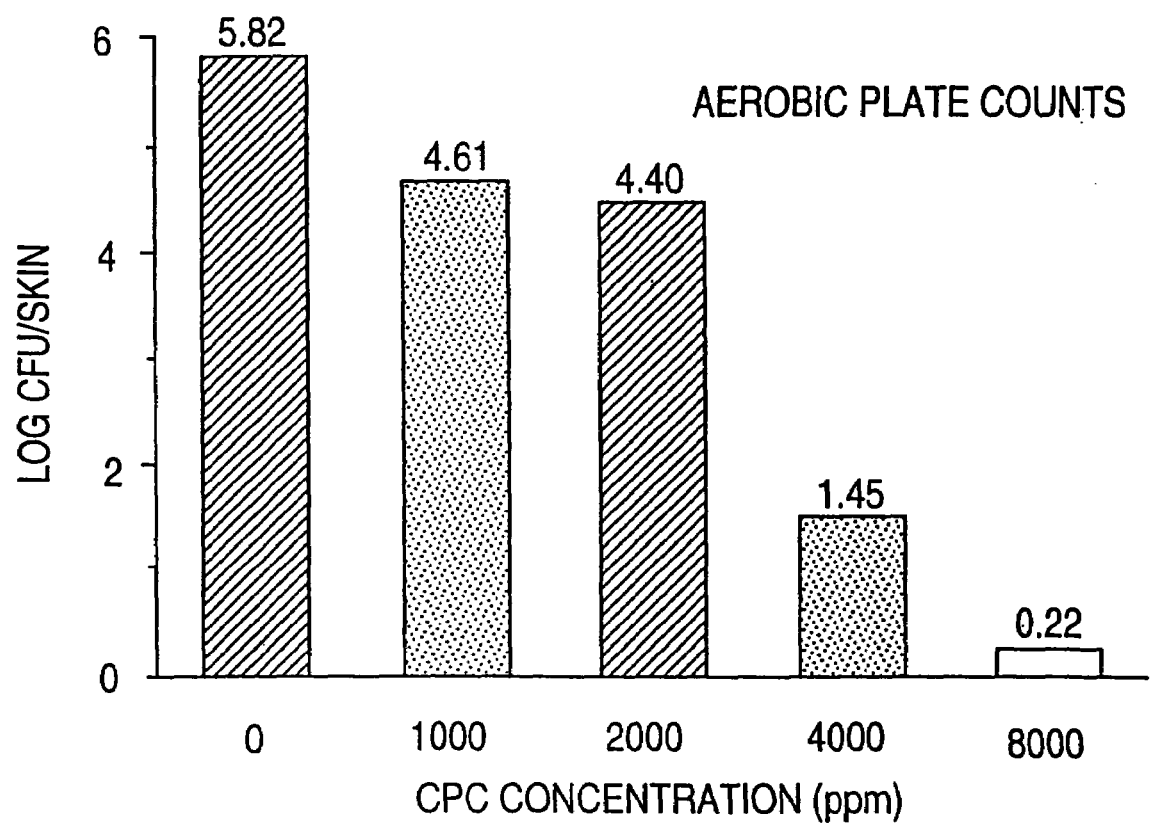
FIG. 2 is a bar graph showing the reduction of viable microorganisms on catfish skin after treatment with CPC in 5% aqueous glycerin on non-selective media.
Figure 3:
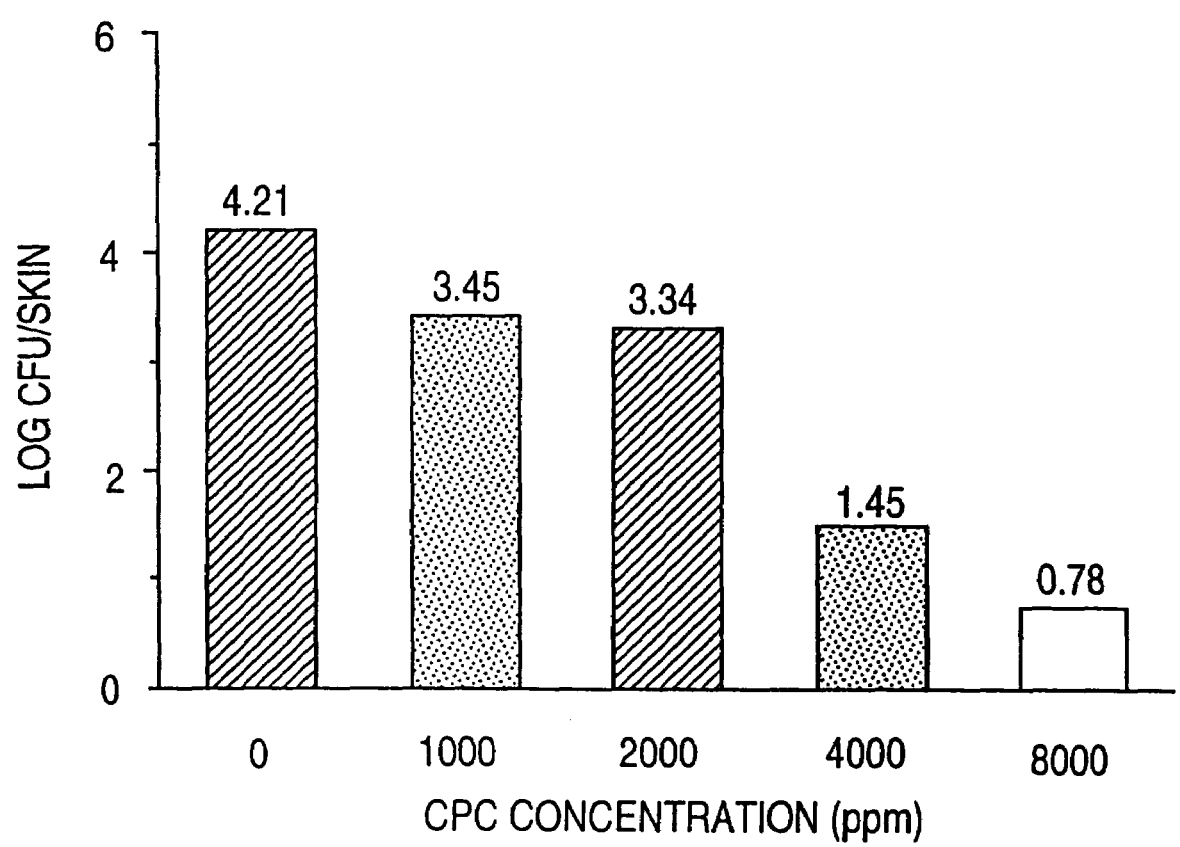
FIG. 3 is a bar graph showing the reduction of viable *S. typhimurium* on catfish skin after treatment with CPC in 5% aqueous glycerin on selective media.
Figure 4:
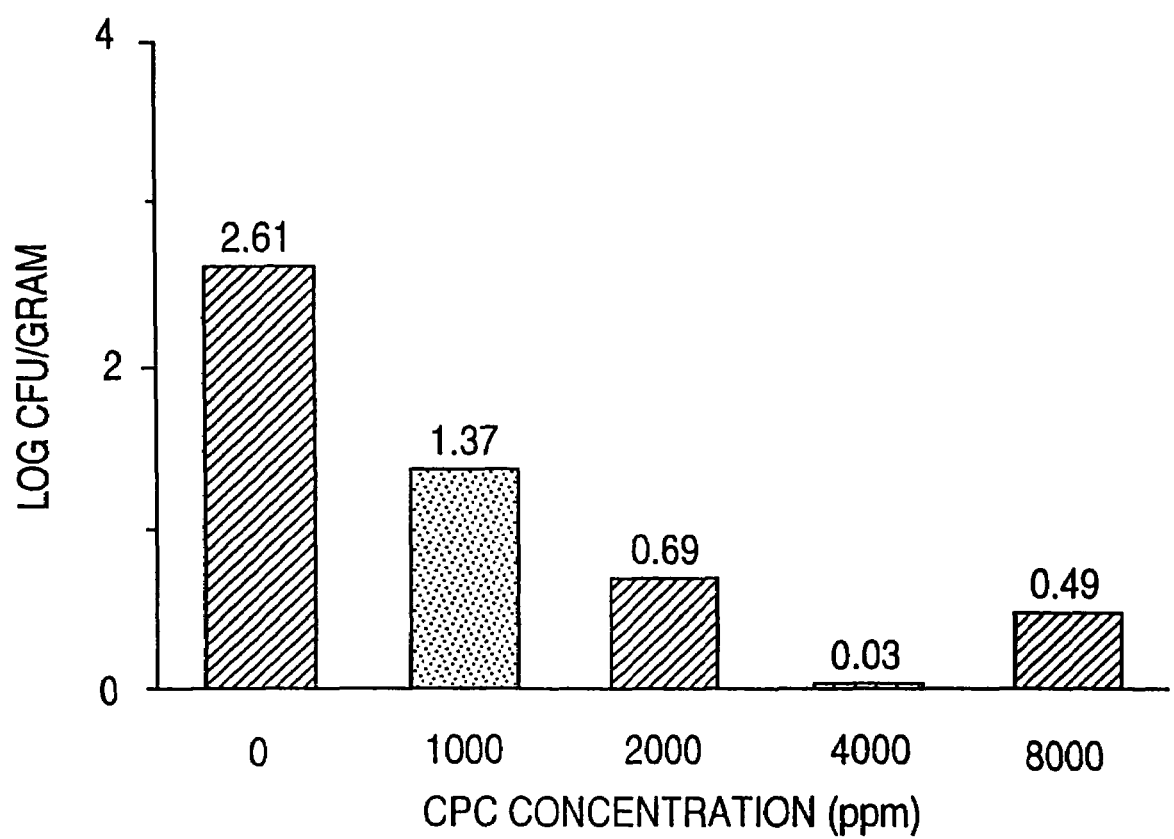
FIG. 4 is a bar graph showing the reduction of viable *S. typhimurium* on black grapes after treatment with CPC in 5% aqueous glycerin.
Figure 5:
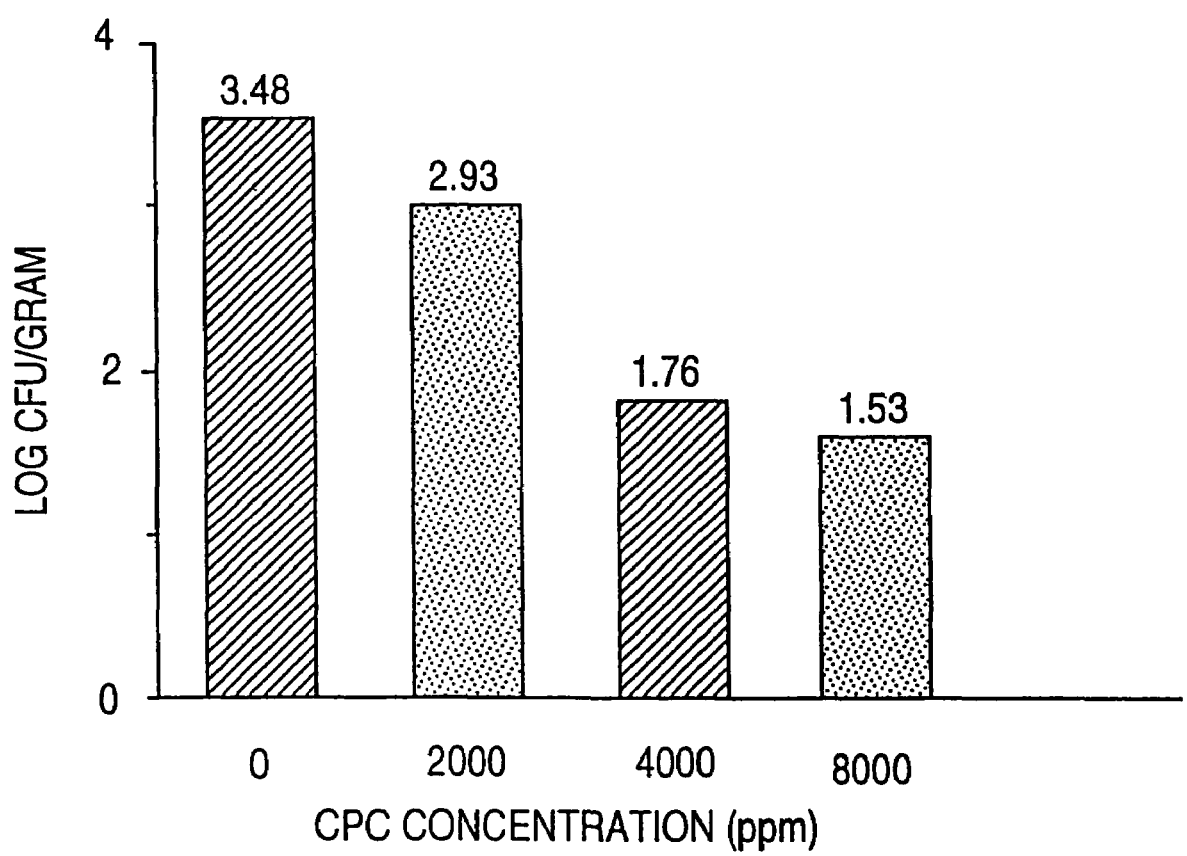
FIG. 5 is a bar graph showing the reduction of viable *S. typhimurium* on broccoli after treatment with CPC in 5% aqueous glycerin.

Inoculum preparation for *S. typhimurium* was performed as described in Example 7 above. Food samples were placed in each well of six-well tissue culture plates. The samples were then inoculated with 5 ml of PBS containing 1 to $2 \times 10^6$ CFU of *S. typhimurium* per ml, with the exception of the background control group that was treated only with 5 ml of PBS. Culture plates with the food samples were incubated (30 min., 35° C.), and then the incubating solution was removed by aspiration. The inoculated samples were treated with 5 ml of the test solution. Sets of three food samples were used for each concentration of test solution, including one set in which the food samples were treated only with 5 ml of 5% (v/v) glycerin in PBS (0 concentration). The plates were incubated at 25° C. with shaking (100 rpm) for 3 min. After incubation, each food sample was prepared and placed in a plastic bag for use with the Stomacher7 400 laboratory blender as described in Example 7 above. A corner of the bag was aseptically cut and the entire contents were transferred to a sterile centrifuge tube, which was then spun for 10 min (12,000 rpm, 20° C.). The pellet was resuspended in 5 ml 0.1% (w/v) peptone/water. One ml of the appropriate dilution was pour plated onto XLD agar for the grape and broccoli experiments and onto both XLD and TSA agar for the catfish in triplicate. After incubation at 37° C. for 24 hour, colonies were counted, corrected for dilution, and reported as CFU/skin for catfish and as CFU/gram for the other food samples. The results of these experiments are shown in FIGS. 2-5. As the catfish were not irradiated, FIG. 2 shows the total aerobic bacterial count on non-selective media whereas FIG. 3 shows only *Salmonella* counts.

Example 11

Effect of Spraying Quaternary Ammonium Compounds on the Reduction of Viable Bacteria on Whole Chickens These experiments tested the effect that spraying QACs on whole chicken carcasses using a commercial sprayer would have on the reduction of viable bacteria. The bacterial inoculating solutions were made as follows: *E. coli* (ATTC # 25922) was grown in brain heart infusion broth (BHI) for 20-24 h and then diluted to a 1:1000 concentration by adding 0.5 ml of *E. coli* culture to 500 ml of physiological saline solution (PSS). *S. typhimurium* was grown in BHI for 20-24 h and then diluted to a 1:5000 concentration by adding 0.1 ml of *S. typhimurium* culture to 500 ml of physiological saline solution (PSS). The CPC treatment solution was prepared to a concentration of 5,000 ppm. Prechill chicken carcasses were obtained from a local poultry processing plant for each trial. The carcasses were placed on a shackle line and 1 ml of the bacterial inoculating solution was sprayed on the breast of the carcass, and 1 ml was sprayed on the back. The bacteria were allowed to attach for 30 min at room temperature. After attachment the carcasses were rinsed on the shackle line with tap water for 20 seconds. The carcasses were divided into groups of ten. For each run, there was a group of ten chickens that was sprayed with 5,000 ppm CPC and there was a group of ten chickens that was sprayed with only tap water. In the *S. typhimurium* tests, there was also a group that was not sprayed after inoculation to evaluate the effect of the spray.

For all of the bacteria, one group of carcasses were treated with the Johnson™ washer for 20 seconds at 60 psi with 35 cups of tap water. After the rinse, the carcasses were allowed to set for 90 seconds, and then rinsed with 20 cups of tap water for 20 seconds at 80 psi. This rinse cycle was repeated either two or three times. The interval of each rinse was also 90 seconds. Another group of carcasses were treated with 5,000 ppm CPC for 20 seconds at 60 psi in the Johnson™ washer, then allowed to set for 90 seconds, and then rinsed with 20 cups of tap water for 20 seconds at 80 psi. This rinse cycle was repeated either two or three times.

After treatment the carcasses were placed in plastic bags and 100 ml of 0.1% buffered peptone water (BPW) was added to each bag. The bags were mechanically shaken and the rinse collected for most probable number (MPN) technique. Petrifilm™ was also employed for evaluation of total aerobic plate counts (TPC). Preexisting (not inoculated) *C. jejuni* was enumerated by the MPN technique and *E. coli* by Petrifilm™.

The results presented below show that the CPC treatment is effective in reducing the number of *C. jejuni*, *E. coli*, and *S. typhimurium*. The wash water for the *S. typhimurium* runs were tested and it was found that CPC in the wash water reduced the *Salmonella* by 1 log. Thus, the kill data presented below for *Salmonella* can be reduced by 1 log.

| BACTERIA PRESENT | | | | |
|---|---|---|---|---|
| | | Water Control | 5,000 ppm CPC | Reduction in $Log_{10}$ |
| C. jejuni | Trial 1 | 2.613 | 0 | 2.613 |
| | Trial 2 | 2.643 | 0.629 | 2.014 |
| E. coli | Trial 1 | 1.974 | 0.386 | 1.588 |
| | Trial 2 | 1.380 | 0.460 | 0.920 |

| | | | | Reduction in $Log_{10}$ CFUs | |
|---|---|---|---|---|---|
| S. typhimurium | No Spray Control | Spray Control | 5,000 ppm CPC | No Spray vs. CPC Treatment | Spray vs. CPC Treatment |
| 1 (Dec, 02, 1996) | 5.342 | 5.039 | 4.295 | 1.047 | 0.744 |
| 2 (Dec. 09, 1996) | 5.304 | 4.932 | 1.977 | 3.327 | 2.955 |
| 3 (Dec. 16, 1996) | 5.001 | 5.154 | 2.606 | 2.395 | 2.548 |
| 4 (Jan. 27, 1997) | 4.72 | 4.48 | 1.03 | 3.69 | 3.45 |
| 5 (Feb. 03, 1997) | 4.185 | 4.212 | 1.426 | 2.76 | 2.79 |

Example 12

Effect of Quaternary Ammonium Compounds on Foodborne Fungi

This study tested the effect of CPC on foodborne fungi. Slant cultures of *Aspergillus flavus* and *Penicillium chrysogenum* were streaked onto a potato dextrose agar (PDA) plates. Thirty minutes after inoculation or 24 h after inoculation (and incubation at room temperature, two round filters (7 mm in diameter) were put on the surface of each plate. CPC solutions of 200 ppm, 1000 ppm, 5000 ppm, and 25,000 ppm or distilled and deionized (DD) water were added to the filters, 10 μl per filter. All plates were incubated lid side up at room temperature for 48 hours. The diameters of the inhibition rings were measure. The results presented below show that CPC is effective against foodborne fungi.

| Concentration of CPC (ppm) | Inhibition Ring (mm) | |
|---|---|---|
| | Immediate Treatment | Delayed Treatment |
| Effect of CPC on *Aspergillus flavus* | | |
| 25,000 | 1.63 | 1.00 |
| 5,000 | 2.00 | 0.92 |
| 1,000 | 0.38 | 1.00 |
| 200 | 0.25 | 0.33 |
| 0 | 0 | 0 |
| Effect of CPC on *Penicillium chrysogenum* | | |
| 25,000 | 4.13 | 1.83 |
| 5,000 | 3.38 | 1.92 |
| 1,000 | 1.00 | 1.67 |
| 200 | 0 | 1.17 |
| 0 | 0 | 0 |

CPC is effective against foodborne fungi tested.

Example 13

Effect of Quaternary Ammonium Compounds on Chicken Carcasses Using Short Application Times In two trials conducted in a commercial broiler processing facility, the Cecureθ formulation (0.2 to 0.5% CPC), that is diluted from a concentrate of CPC containing CPC (40%), propylene glycol (57%) and water (3%), all components on a weight to weight basis, was used to treat post-chill chicken carcasses. In these studies, the final rinse cabinet or "fecal failure" cabinet that is positioned prior to grading and packaging, but after immersion chilling, was modified for application of the CPC formulation. Cabinet modifications included changing the nozzles to allow for only small volumes (1 to 6 ounces) of the formulation per carcass, and modification of the spray pattern on the carcasses to allow for total coverage of maximum surface area. In addition, the length of the cabinet was extended and cabinet exhaust mechanisms were installed. The concentrated Cecureθ formulation was either diluted to the correct use concentration at the point of direct application to the carcass, or was diluted and held in large vessels prior to application. The dilute Cecureθ solution was applied to each carcass for about 1.5 seconds. The temperature of the solution was at ambient room temperature or slightly above or below depending on storage conditions.

After carcass treatment with the dilute Cecureθ, the carcasses were allowed to drip for approximately 3 minutes prior to microbiological sampling. Carcasses were sampled using a whole carcass rinse technique in 400 mL of buffered peptone water. Samples were evaluated for *Campylobacter, Salmonella*, non-toxin producing *E. coli*, and aerobic plate count that estimates the total organisms. Control carcasses were also evaluated for these same organisms, but these carcasses were collected, just prior to the modified fecal failure cabinet. In both trials, *Campylobacter, E. coli*, and aerobic (total aerobic bacteria) plate counts were significantly reduced by greater than 99%. In both trials, the incidence of *Salmonella* was significantly reduced to less than 10% positive while control carcass *Salmonella* incidence rates were in some cases greater than 60%.

The foregoing description of the preferred embodiments of the present invention was presented for illustrative purposes and not meant to limit the invention to specific compositions used in the examples because various modifications to the disclosed invention are possible in light of the above teachings. The present invention is based upon the discovery that QAC significantly prevents and reduces bacterial contamination by a broad spectrum of foodborne microbial contamination than was previously known. The concentrated QAC formulation provides many advantages for use on a large scale in a food processing plant. The invention is intended to cover alternatives, modifications and equivalents, which may be included within the spirit and scope of the invention as defined by the appended claims.

We claim:

1. A method, comprising:
   (1) providing a concentrated quaternary ammonium compound solution comprising: a quaternary ammonium compound with a concentration from greater than about 10% by weight; and at least one solubility enhancing agent, wherein said quaternary ammonium compound is selected from the group consisting of:
   an alkylpyridinium salt represented by the structural formula (I):

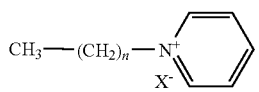

wherein n is 9-21; and X is a halide, and an alkylalicyclic ammonium salt represented by the structural formula (III):

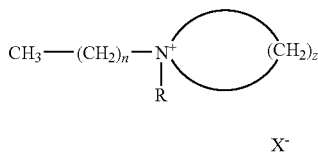

X⁻ wherein n is 9-21; Z is 4-5; R is selected from the group consisting of CH3 and C2H5; and X is a halide;
(2) diluting said concentrated quaternary ammonium compound solution; and
(3) applying said solution to a food product, wherein said food product comprises seafood.

2. The method of claim 1, wherein said seafood comprises fish.

3. The method of claim 2, wherein said fish comprises catfish.

4. The method of claim 1, wherein step (3) comprises: applying an amount of said solution effective to remove *E. coli* 0157:H7 from said food product.

5. The method of claim 1, wherein said quaternary ammonium compound is an alkylpyridinium salt represented by the structural formula (I).

6. The method of claim 5, wherein said quaternary ammonium compound is cetylpyridinium chloride.

7. The method of claim 1, wherein said at least one solubility enhancing agent is propylene glycol.

8. The method of claim 1, wherein said quaternary ammonium compound is cetylpyridinium chloride; and
said at least one solubility enhancing agent is propylene glycol.

9. The method of claim 1, wherein step (3) comprises: applying an amount of said solution effective to remove microbial contamination from said food product, said microbial contamination comprising one or more microorganisms selected from the group consisting of the genus *Staphylococcus, Streptococcus, Campylobacter, Arcobacter, Listeria, Aeromonas, Bacillus, Salmonella,* non-toxin-producing *Escherichia,* and pathogenic toxin-producing *Escherichia.*

10. A method, comprising:
(1) providing a concentrated quaternary ammonium compound solution comprising: a quaternary ammonium compound with a concentration from greater than about 10% by weight; and at least one solubility enhancing agent, wherein said quaternary ammonium compound is selected from the group consisting of:
an alkylpyridinium salt represented by the structural formula (I):

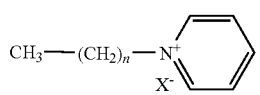

wherein n is 9-21; and X is a halide, and
an alkylalicyclic ammonium salt represented by the structural formula (III):

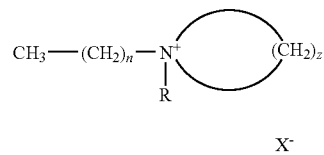

X⁻ wherein n is 9-21; Z is 4-5; R is selected from the group consisting of CH₃ and C₂H₅, and X is a halide; and
(2) applying said solution to a food product, wherein said food product comprises seafood.

11. The method of claim 10, wherein step (2) comprises: applying an amount of said solution effective to remove *E. coli* 0157:H7 from said food product.

12. The method of claim 10, wherein said quaternary ammonium compound is an alkylpyridinium salt represented by the structural formula (I).

13. The method of claim 12, wherein said quaternary ammonium compound is cetylpyridinium chloride.

14. The method of claim 10, wherein said at least one solubility enhancing agent is propylene glycol.

15. The method of claim 10, said quaternary ammonium compound is cetylpyridinium chloride and said at least one solubility enhancing agent is propylene glycol.

16. The method of claim 10, wherein step (2) comprises:
applying an amount of said solution effective to remove microbial contamination from said food product, said microbial contamination comprising one or more microorganisms selected from the group consisting of the genus *Staphylococcus, Streptococcus, Campylobacter, Arcobacter, Listeria, Aeromonas, Bacillus, Salmonella,* non-toxin-producing *Escherichia,* and pathogenic toxin-producing *Escherichia.*

17. The method of claim 10, wherein said seafood comprises fish.

18. The method of claim 17, wherein said fish comprises catfish.

19. The method of claim 1, wherein step (1) comprises:
providing said concentrated quaternary ammonium compound solution comprising:
said quaternary ammonium compound with said concentration from greater than about 15% by weight; and
said at least one solubility enhancing agent.

20. The method of claim 10, wherein step (1) comprises:
providing said concentrated quaternary ammonium compound solution comprising:
said quaternary ammonium compound with said concentration from greater than about 15% by weight; and
said at least one solubility enhancing agent.

21. The method of claim 1, wherein step (2) comprises: diluting said concentrated quaternary ammonium compound solution so that said quaternary ammonium compound is present in said solution in a weight percent substantially within a range of from approximately 0.1 percent to approximately 1 percent.

* * * * *